United States Patent
Saenger et al.

(10) Patent No.: US 6,361,506 B1
(45) Date of Patent: Mar. 26, 2002

(54) INCREMENTAL VARUS/VALGUS AND FLEXION/EXTENSION MEASURING INSTRUMENT

(75) Inventors: Paul L. Saenger, Asheville, NC (US); Richard J. Kana, Lexington; Charles H. Perrone, Jr., Austin, both of TX (US)

(73) Assignee: Sulzer Orthopedics Inc., Austin, TX (US)

(*) Notice: Subject to any disclaimer, the term of this patent is extended or adjusted under 35 U.S.C. 154(b) by 0 days.

(21) Appl. No.: 09/620,432

(22) Filed: Jul. 20, 2000

(51) Int. Cl.[7] .............................................. A61B 5/103
(52) U.S. Cl. ........................ 600/587; 33/512; 606/53; 606/102
(58) Field of Search ................................. 600/587, 595; 606/53, 79, 86, 88, 89, 102; 33/511, 512

(56) References Cited

U.S. PATENT DOCUMENTS

| | | | |
|---|---|---|---|
| 1,590,499 A | * 6/1926 | Cozad | 600/595 |
| 4,226,025 A | * 10/1980 | Wheeler | 33/512 |
| 5,188,121 A | * 2/1993 | Hanson | 600/594 |
| 5,376,093 A | * 12/1994 | Newman | 606/88 |
| 5,469,862 A | * 11/1995 | Kovacevic | 600/595 |
| 5,776,082 A | * 7/1998 | Riley et al. | 600/594 |
| 5,810,827 A | * 9/1998 | Haines et al. | 606/80 |
| 6,048,322 A | * 4/2000 | Kushida | 600/587 |

OTHER PUBLICATIONS

Mullen, M.P., et al., "Natural–Knee Unimcompartmental Replacement System", Surgical Technique Brochure, Intermedics Orthopedics, Inc. (1994).

Mullen, M.P., et al., "The Intermedics Natural–Knee Unicompartmental Replacement", Surgical Technique Brochure, Intermedics Orthopedics, Inc. (1990).

* cited by examiner

Primary Examiner—Eric F. Winakur
Assistant Examiner—Charles Marmor, II
(74) Attorney, Agent, or Firm—Philip S. Lyren

(57) ABSTRACT

A surgical measuring instrument includes a caliper having pin apertures formed therein for mounting on surgical pins in a first skeletal member. An adaptor includes pin apertures on a first portion for mounting on the surgical pins when the caliper is removed, and includes adaptor pins extending from a second portion for engagement with the caliper. A rod is connected to the caliper for indicating alignment and flexibility of a second skeletal member relative to the first skeletal member.

21 Claims, 4 Drawing Sheets

INCREMENTAL VARUS/VALGUS AND FLEXION/EXTENSION MEASURING INSTRUMENT

BACKGROUND

The disclosures herein related generally to skeletal joint surgery and more particularly to an instrument for measuring both the alignment and the flexion of one skeletal member relative to another skeletal member.

Instruments are used to satisfy a surgical desire to accurately measure the angle of a varus or valgus knee and/or to measure the extent of a knee in flexion and extension during a uni or total knee replacement surgery.

It is normal practice for a surgeon to review patient x-rays prior to either a uni or total knee replacement surgery. This review gives the surgeon direction and aids in determining the amount of, if any, angular/alignment correction to establish in the patient's knee during the surgical procedure.

Although a surgeon may realize how much correction is required, it is sometimes difficult to determine if that degree of correction has been obtained in surgery. Several types of devices are available to determine alignment but few are available to measure alignment before implantation of a knee replacement and then again after the implantation is complete, thus, determining the amount of incremental change.

There are numerous devices of varying complexity that a surgeon may use to measure the degree of deformity in a knee. Devices like a simple Goniometer, which are commonly used to measure angles on an x-ray to more complex surgical devices that are used on the human anatomy. Most instruments will violate the intramedullary canal which is undesirable.

A Goniometer is a dual armed instrument for measuring angles. One arm has a pointer, the other a protractor scale. A pivot, that provides enough friction to stabilize the instrument for easy reading, joins these arms.

Sulzer Orthopedics Inc. offers an Uni-Knee Alignment Checker, part number 6190-00-117, which is a surgical instrument for measuring anatomical alignment of a knee in extension. Other knee systems and orthopedic companies offer a similar type instrument.

Therefore, what is needed is an alignment and flexibility measuring device to accurately measure the angle of a varus or valgus knee and to measure the flexion and extension of the knee during a uni or total knee replacement surgery.

SUMMARY

One embodiment, accordingly, provides an instrument which is useful for measuring the "before" resection alignment of a joint and the "after" resection alignment of the joint, and to also for measuring the flexion and extension of a knee during a uni or total knee replacement surgery. To this end, a knee surgery instrument includes an adaptor having pin apertures formed therein for receiving surgical pins, and also includes adaptor pins extending therefrom. A caliper may be mounted on the adaptor pins and on the surgical pins in a first skeletal member. A rod is connected to the caliper for indicating alignment and flexibility of a second skeletal member relative to the first skeletal member.

A principal advantage of this embodiment is that the instrument and the associated procedure are minimally invasive, provides measurement for varus and/or valgus deformities, provides flexion and extension measurement, provides alignment measurement before and after implantation, and allows an expansive range of measurement.

BRIEF DESCRIPTION OF THE DRAWING FIGURES

DETAILED DESCRIPTION

Figure 1:
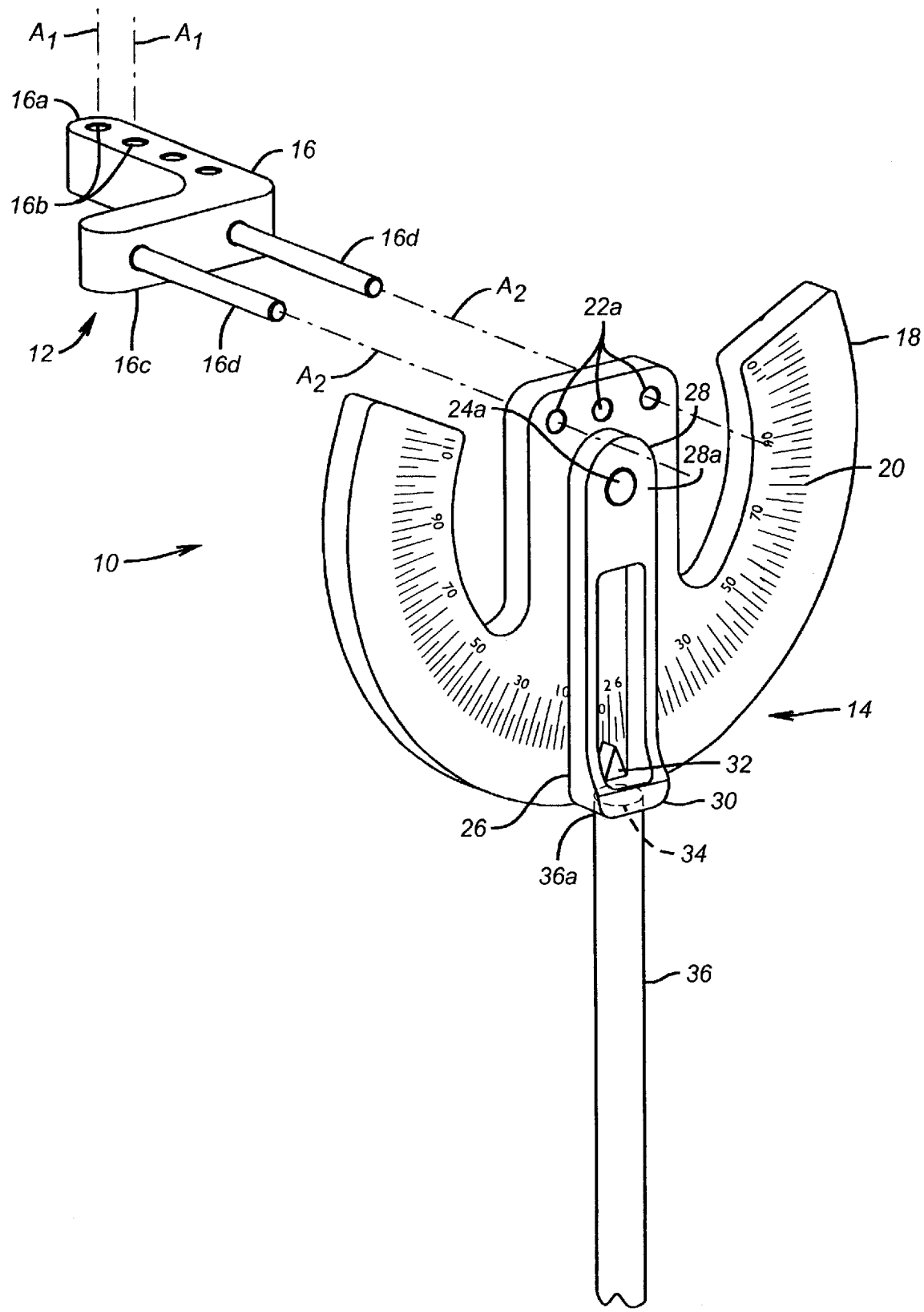
FIG. 1 is an isometric view illustrating an embodiment of an instrument for measuring alignment and flexion and extension.
Figure 2:
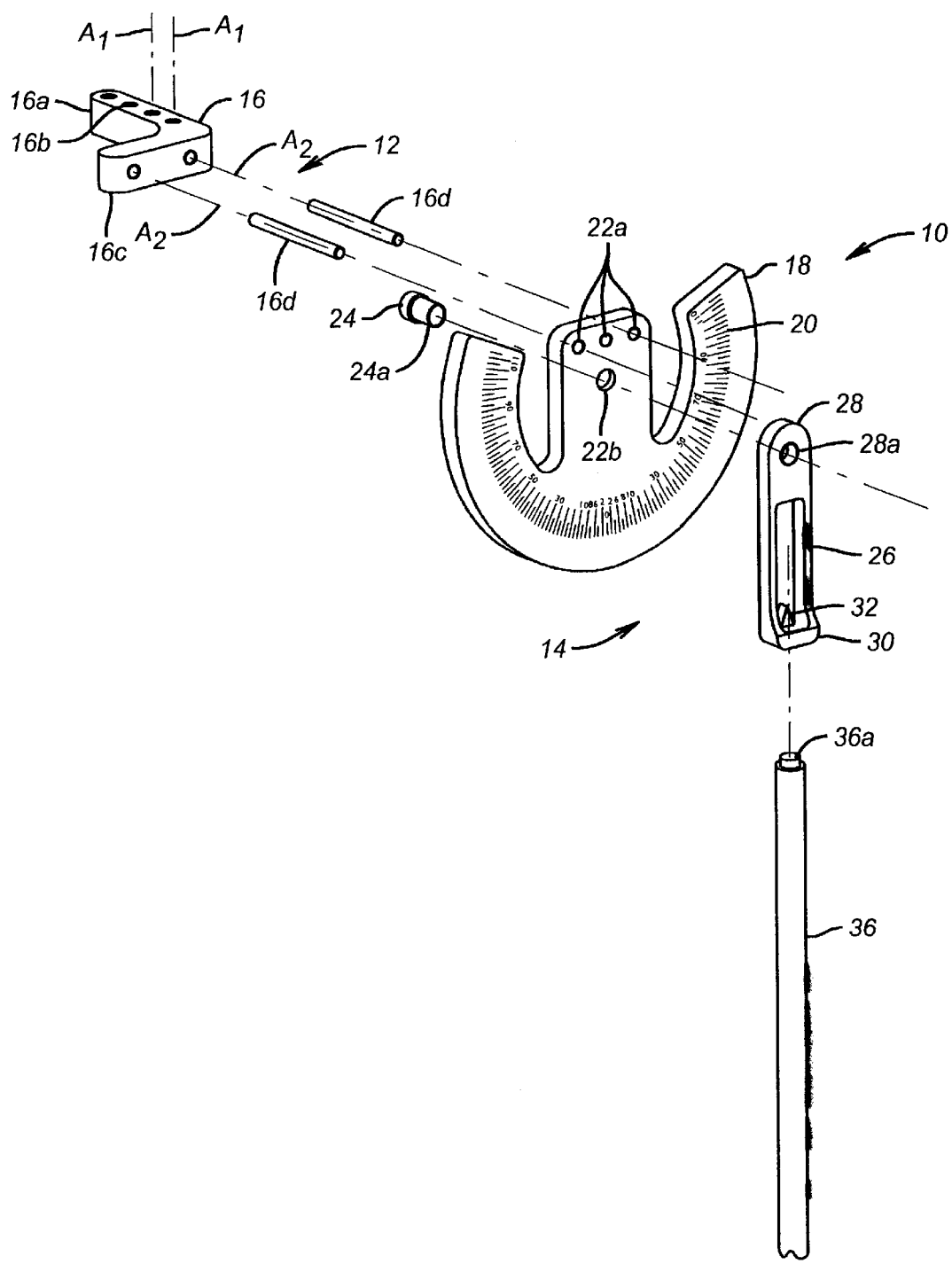
FIG. 2 is an exploded view illustrating the instrument of FIG. 1.

A surgical measuring instrument is generally designated 10 in FIGS. 1 and 2, and includes an adaptor assembly 12 and a measurement assembly 14.

The adapter assembly 12 includes an adaptor 16 which is generally "L" shaped and includes a first portion 16a having a plurality of pin apertures 16b formed therein. Each of the pin apertures 16b have an axis designated A1. The adaptor assembly 12 also includes a second portion 16c which is disposed substantially at a right angle (90?) relative to first portion 16a. The second portion 16c also includes a plurality of adaptor pins 16d extending therefrom. Each of the adaptor pins 16d have an axis designated A2, which is disposed substantially at a right angle relative to the axis designated A1, and substantially parallel to first portion 16a.

The measurement assembly 14 includes a caliper 18 having a scale 20 thereon. The scale 20 is engraved with markings similar to a protractor. Angular increment marks are engraved every two degrees about a central pivot point. The ranges of incremental marks are from 0 to 112 degrees, both counter-clockwise and clockwise, totaling a span of 224 degrees. Numeric markings to identify the angle are engraved from 0 to 14 degrees in four-degree increments and in 20-degree increments from 30 to 110 degrees.

Several apertures are formed in caliper 18. Three of the apertures 22a are spaced equidistantly apart to receive surgical pins (discussed below) and to receive the adaptor pins 16d. Another aperture 22b is provided to receive a pivot pin 24.

A pointer member 26 includes a first end 28 having an aperture 28a formed therein for receiving an extended end 24a of the pivot pin 24. In this manner, the pointer member 26 is mounted on caliper 18 for bidirectional pivotal movement relative to scale 20. A second end 30 of pointer member 26 includes an indicator 32 and a threaded rod receiving aperture 34. A rod 36 includes an end 36a which is connected to pointer member 26 by means of aperture 34. In this manner, the rod 36 is movable with the pointer member 26. Pivot pin 24 provides enough friction between pointer member 26 and caliper 18 to stabilize the pointer member 26 for easy reading relative to scale 20.

Figure 3:
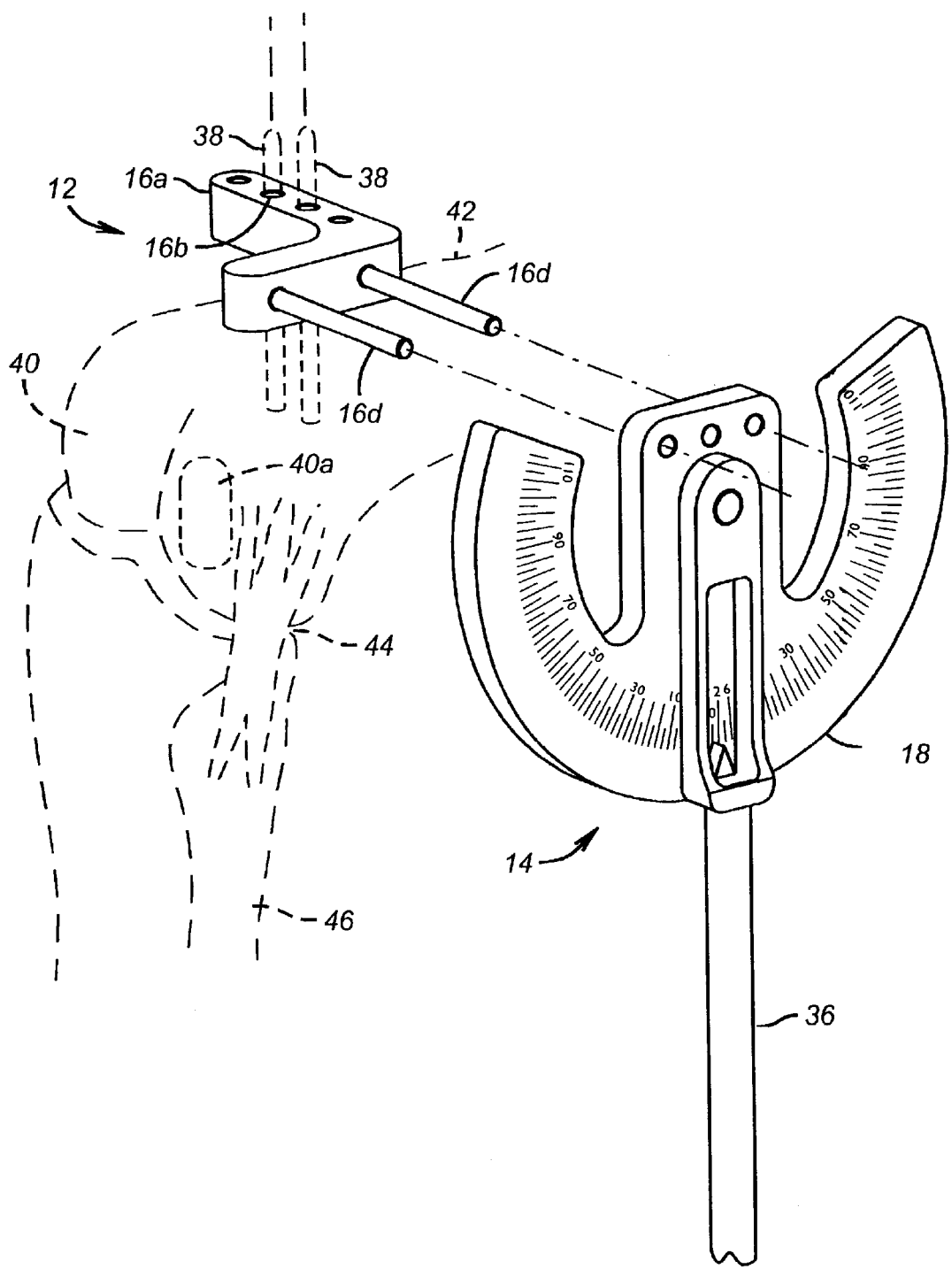
FIG. 3 is an isometric view illustrating the instrument of FIG. 1 positioned for measuring flexion and extension of a knee joint.
Figure 4:
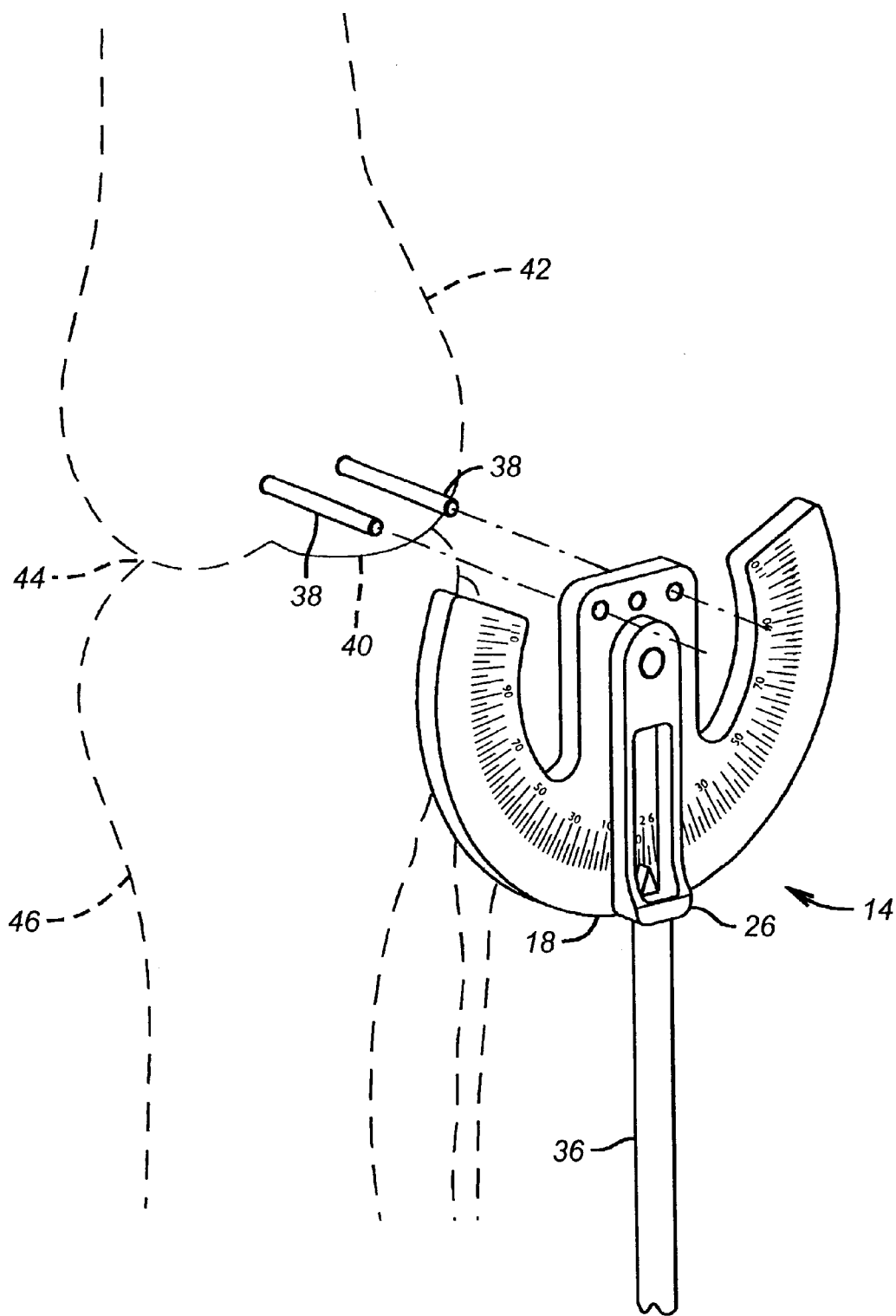
FIG. 4 is an isometric view illustrating the instrument of FIG. 1 positioned for measuring varus/valgus alignment of the knee joint.

During a uni-knee procedure, 'surgical pins 38, FIG. 3, are located in the distal end 40 of a first skeletal member such as a femur 42. This is done, as it is well known, for the purpose of locating a saw guide (not shown) and establishing a cutting depth for resecting a portion 40a the distal end 40 of the femur 42. Therefore, with the pins 38 in place, they may also be used for mounting the caliper 18, FIG. 4, including the pointer member 26 and the rod 36, adjacent a knee joint 44 which connects the femur 42 to a second skeletal member, i.e. a tibia 46. In this position the measurement assembly 14 measures anatomical varus/valgus alignment of the knee joint 44 while in extension. Measurement may be taken before the surgeon makes any bone resections and again during trial reduction or after the implants have been placed.

In addition, the adaptor assembly 12 may be mounted on the surgical pins 38, FIG. 3, by mounting first portion 16a on the pins 38 so that the pins 38 extend through the pin apertures 16b. The adaptor assembly 12 may be inverted so as to position the adaptor pins 16d to either the medial or lateral side of the knee joint 44. This feature also permits adaptor assembly 12 to be used on either a right or a left knee. The measurement assembly 14 may then be located onto the two adaptor pins 16d of the adaptor assembly 12. The adapter assembly 12 references the pins 38 in the femur as mentioned above. When the measurement assembly 14 is positioned in this way, measurement may be taken of the extension and flexion of the knee joint 44. This measurement may also be taken before, during and after the surgeon has made bone resection and implant placements.

The pointer member 26, pivots-about pivot pin 24 and indicates the angle of measurement. Attached to the pointer member 26 is the rod 36 which is used to align with the patient's natural anatomy. Once the surgeon makes the alignment, the pointer member 26 indicates the measurement. Pivot pin 24 secures the scale 20 and the pointer member 26 together. The pivot pin 24 allows free rotation of the pointer member 26 and the rod 36 so that anatomic alignment may be measured. The adaptor 16 has four apertures 16b positioned to match up to pins 38 that have been located in the femur 42. Only two apertures 6b are used at any one time. The additional apertures 16b permit the surgeon to shift the adapter 16 either closer to, or further away from, the soft tissues of the knee joint 44.

As it can be seen, the principal advantages of these embodiments are that the procedure is minimally invasive. That is, drilling a relatively large hole into the intramedullary canal is not required. The canal is not violated, and the patella does not have to be displaced or inverted. The instrument measures varus and/or valgus deformities. Typical devices measure corrected alignment, whereas this instrument will measure alignment both before-and after surgical correction. The instrument also measures flexion and extension. The surgeon, without any form of a measuring device, often estimates flexion and extension. That estimation is sometimes unclear if not measured both before the procedure and then again after the completion of the procedure.

In addition, the instrument measures alignment before and after implantation. This instrument may use the same references that are used to locate the positioning of the implant. Correction of the knee can be measured incrementally by knowing the alignment prior to beginning the surgical procedure. Therefore, the instrument affords the surgeon quick and accurate visualization of the exact increment of correction created by the surgical procedure.

An extensive range of measurement is possible. The caliper can measure from a relatively small range of extension to a substantially large range of flexion, respectively, from about −5? to about 135?. The instrument may be used for a minimally invasive uni-knee procedure as well as a total knee and other procedures where alignment, flexion and extension measurement are required.

A surgeon often realizes and predetermines through review of patient x-rays how much correction is required in the joint alignment. Once this increment is known, most systems have cutting blocks and/or alignment type devices to help the surgeon increment bone resections.

The uniqueness of this instrument is its ability to measure the "before" alignment of a joint and then the "after" alignment of the joint; before any bone resection is made, and again during and after trial reduction of the joint. The measurement is an incremental measurement of surgical correction and is not totally dependent on the patients anatomy.

As a result, one embodiment provides a surgical measuring instrument including a caliper having pin apertures formed therein for mounting on surgical pins in a first skeletal member and an adaptor having pin apertures formed in a first adaptor portion for mounting on the surgical pins. Adapter pins extend from a second adaptor portion for engagement with the caliper pin apertures. A rod is connected to the caliper for indicating alignment of a second skeletal member relative to the first skeletal member when the caliper is mounted on the surgical pins, and for measuring flexibility of the second skeletal member when the caliper is mounted on the adapter pins.

Another embodiment provides a method of measuring alignment and flexibility of a skeletal joint accomplished by inserting surgical pins in a first skeletal member and mounting a caliper on the surgical pins. The caliper includes a rod connected for measuring alignment of a second skeletal member relative to the first skeletal member. The rod and caliper are removed from the surgical pins. An adapter is mounted on the surgical pins. The adaptor includes adaptor pins extending therefrom. The caliper is mounted on the adaptor. The caliper includes the rod for measuring flexibility of the second skeletal member relative to the first skeletal member.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. An alignment and flexibility measuring instrument comprising:
   a caliper having pin apertures formed therein for mounting on surgical pins in a first skeletal member;
   an adaptor having pin apertures formed in a first adaptor portion for mounting on the surgical pins, and having adaptor pins extending from a second adaptor portion for engagement with the caliper pin apertures; and
   a rod connected to the caliper for indicating alignment of a second skeletal member relative to the first skeletal member when the caliper is mounted on the surgical pins, and for measuring flexibility of the second skeletal member relative to the first skeletal member when the caliper is mounted on the adaptor pins.

2. The instrument as defined in claim 1 wherein the caliper includes a scale.

3. The instrument as defined in claim 2 wherein the caliper includes a pointer movable relative to the scale.

4. The instrument as defined in claim 3 wherein the rod is connected to the pointer and movable therewith.

5. The instrument as defined in claim 1 wherein the first portion of the adaptor includes the pin apertures extending in a first direction.

6. The instrument as defined in claim 5 wherein the second portion of the adaptor includes the adaptor pins extending in a second direction, different than the first direction.

7. The instrument as defined in claim 6 wherein the second direction is about 90? relative to the first direction.

8. The instrument as defined in claim 7 wherein the second portion of the adaptor is disposed at about a 90? angle relative to the first portion of the adaptor.

9. A knee surgery instrument comprising:
- an adaptor having pin apertures formed therein for receiving a plurality of surgical pins in a first skeletal member, and having adaptor pins extending from the adaptor for receiving a caliper;
- the caliper having pin apertures formed therein for mounting on the surgical pins and for mounting on the adaptor pins; and
- a rod mounted on the caliper for indicating alignment and flexibility of a second skeletal member relative to the first skeletal member.

10. The instrument as defined in claim 9 wherein the caliper includes a scale.

11. The instrument as defined in claim 10 wherein the caliper includes a pointer movable relative to the scale.

12. The instrument as defined in claim 11 wherein the rod is connected to the pointer and movable therewith.

13. The instrument as defined in claim 9 wherein the pin apertures are formed in a first portion of the adapter, the pin apertures extending in a first direction.

14. The instrument as defined in claim 13 wherein the adaptor pins extend from a second portion of the adaptor, the adaptor pins extending in a second direction, different from the first direction.

15. The instrument as defined in claim 14 wherein the second direction is about 90? relative to the first direction.

16. The instrument as defined in claim 15 wherein the second portion of the adaptor is disposed at about a 90? angle relative to the first portion of the adaptor.

17. A method of measuring alignment and flexibility of a skeletal joint comprising the steps of:
- inserting surgical pins in a first skeletal member;
- mounting a caliper on the surgical pins, the caliper including a rod connected thereto for measuring alignment of a second skeletal member relative to the first skeletal member;
- removing the rod and caliper;
- mounting an adaptor on the surgical pins, the adaptor including adaptor pins extending therefrom; and
- mounting the caliper on the adaptor, the caliper including the rod for measuring flexibility of the second skeletal member relative to the first skeletal member.

18. The method as defined in claim 17 wherein the step of mounting a caliper includes the steps of pivotally connecting a pointer to the caliper and mounting the rod on the pointer.

19. The method as defined in claim 17 further comprising the step of providing a scale on the caliper adjacent the pointer.

20. A method of measuring alignment and flexion of a skeletal joint comprising the steps of:
- inserting surgical pins in a first skeletal member;
- mounting a caliper on the surgical pins, the caliper including a rod connected thereto for measuring alignment of a second skeletal member relative to the first skeletal member;
- removing the rod and caliper;
- resecting at least one of the skeletal members;
- again mounting the caliper on the surgical pins, the caliper including the rod for measuring alignment of the second skeletal member relative to the first skeletal member;
- again removing the rod and caliper;
- mounting an adaptor on the surgical pins, the adaptor including adaptor pins extending therefrom; and
- mounting the caliper on the adaptor, the caliper including the rod for measuring flexibility of the second skeletal member relative to the first skeletal member.

21. A surgical measuring instrument comprising:
- an adaptor having a first portion and a second portion, the first portion including a plurality of pin receiving apertures formed therein, the second portion being formed at a right angular relationship with the first portion and having a plurality of adaptor pins extending therefrom;
- a caliper having a scale thereon, the caliper including a plurality of adaptor pin apertures formed therein;
- a pointer pivotally mounted on the caliper for bidirectional movement relative to the scale; and
- an alignment rod connected to the pointer for movement therewith.

* * * * *